United States Patent
Schmitt et al.

(10) Patent No.: US 12,310,342 B2
(45) Date of Patent: May 27, 2025

(54) CLIMATE SYSTEM

(71) Applicant: Bühler Insect Technology Solutions AG, Uzwil (CH)

(72) Inventors: Eric Holland Schmitt, Antwerp (BE); Jaco Jansen, Breda (NL); Kees Wilhelmus Petrus Aarts, Vught (NL); Maurits Petrus Maria Jansen, Bavel (NL); Vincent De Gelder, Gorinchem (NL)

(73) Assignee: Bühler Insect Technology Solutions AG, Uzwil (CH)

( * ) Notice: Subject to any disclaimer, the term of this patent is extended or adjusted under 35 U.S.C. 154(b) by 231 days.

(21) Appl. No.: 17/596,068

(22) PCT Filed: Jun. 3, 2020

(86) PCT No.: PCT/EP2020/065293
§ 371 (c)(1),
(2) Date: Dec. 2, 2021

(87) PCT Pub. No.: WO2020/245158
PCT Pub. Date: Dec. 10, 2020

(65) Prior Publication Data
US 2022/0295737 A1    Sep. 22, 2022

(30) Foreign Application Priority Data
Jun. 3, 2019 (EP) .................... 19 17 7861

(51) Int. Cl.
*A01K 67/30* (2025.01)
(52) U.S. Cl.
CPC .................... *A01K 67/30* (2025.01)
(58) Field of Classification Search
CPC ............ A01K 67/033; A01K 1/0047
(Continued)

(56) References Cited

U.S. PATENT DOCUMENTS 4,572,427 A * 2/1986 Selfridge ............... B01L 7/00
236/44 C
5,113,799 A * 5/1992 Carr .................. A01K 67/033
119/6.5
(Continued)

FOREIGN PATENT DOCUMENTS

CN      101657091 A     2/2010
CN      101675014 A     3/2010
(Continued)

OTHER PUBLICATIONS

Wermac Definition of the use of Expansion Joints Bellows in Piping Systems (https://www.wermac.org/specials/expansion_joint.html) (Year: 2010).*

*Primary Examiner* — Tye William Abell
*Assistant Examiner* — Maria E Graber
(74) *Attorney, Agent, or Firm* — Colson Law Group, PLLC

(57) ABSTRACT

The present invention concerns a system for providing conditioned air to a room for rearing insect larvae. The system comprises crates for storing the insect larvae, wherein the crates are stackable to form a vertical column and wherein the crates comprise lateral cutouts disposed on opposite sides. An air inlet duct for providing conditioned air to the crates is disposed in a vertical direction and comprises at least one nozzle for each crate in a column. The position of the at least one nozzle corresponds to the position of the lateral cutout of the respective crate. The system further comprises an air outlet duct, wherein the air outlet duct is disposed in a vertical direction and wherein the air outlet duct is disposed on a side of the stacked crates opposite to the air inlet duct.

9 Claims, 6 Drawing Sheets

(58) Field of Classification Search
 USPC .......................................................... 119/6.5
 See application file for complete search history.

(56) References Cited

U.S. PATENT DOCUMENTS

| | | | | |
|---|---|---|---|---|
| 5,178,094 | A * | 1/1993 | Carr ..................... | A01K 67/033 |
| | | | | 119/6.5 |
| 5,819,685 | A * | 10/1998 | Kappelt ............... | A01K 67/033 |
| | | | | 119/6.5 |
| 8,602,837 | B1 * | 12/2013 | Allan ..................... | A01K 47/00 |
| | | | | 449/27 |
| 9,302,949 | B2 * | 4/2016 | Milin ...................... | C05F 17/05 |
| 9,629,339 | B2 * | 4/2017 | Newton ................... | A01K 5/00 |
| 2011/0139075 | A1 * | 6/2011 | Shapiro Ilan ........ | A01K 67/033 |
| | | | | 119/6.5 |
| 2012/0187041 | A1 * | 7/2012 | Popa .................... | A01K 67/033 |
| | | | | 119/6.5 |
| 2016/0066552 | A1 | 3/2016 | Arsiwalla et al. | |

FOREIGN PATENT DOCUMENTS

| | | | | |
|---|---|---|---|---|
| CN | 109430101 | A | 3/2019 | |
| EP | 2986107 | A1 | 2/2016 | |
| JP | 2006046766 | A | 2/2006 | |
| JP | 2008096049 | A | 4/2008 | |
| JP | 2010002069 | A | 1/2010 | |
| JP | 2011133129 | A | 7/2011 | |
| JP | 2012208934 | A | 10/2012 | |
| JP | 2018120275 | A | 8/2018 | |
| WO | WO-2014171829 | A1 * | 10/2014 | ........... A01K 1/0047 |
| WO | WO-2015023178 | A1 * | 2/2015 | ........... A01K 67/033 |
| WO | WO-2019022596 | A1 * | 1/2019 | ........... A01K 1/0047 |
| WO | 2019/059760 | A1 | 3/2019 | |

* cited by examiner

CLIMATE SYSTEM

The present invention is directed towards a system for providing conditioned air to a room for rearing insect larvae.

When rearing insect larvae, it is important to homogenously provide fresh conditioned air, i.e. air with a set temperature, moisture, $O_2$ and $CO_2$ content, to all insect larvae, in particular due to the heat, moisture and $CO_2$ production of the larvae and the substrate and to establish an optimal growth climate. In conventional rearing facilities insect larvae grow on a substrate in crates. In other words, inside the crates there is a biomass consisting of larvae and a substrate, which may comprise feed for larvae, insect droppings, insect skin parts, microorganisms, etc. Air circulation is obtained by fans. This, however, is only feasible for a low-density scenario. If more crates per room are used, the effectiveness of the air circulation is reduced and at some point the limits of such a system are reached. In conventional systems, crates are used which do however not yield optimal homogenous climate conditions for all scenarios.

It is therefore desirable to provide a system which allows high-density rearing of larvae in large quantities by improving the air circulation in the room. In particular, a directed airflow over each individual crate and conditioned air to optimise the biomass to air energy transfer shall be provided. Furthermore, the air has to be extracted from the room without allowing heat and moisture to build up in order to have an optimal growth climate for the insect larvae.

These objects are solved by the present invention as defined in the claims.

In particular, the present invention concerns a system for providing conditioned air to a room for rearing insect larvae. The system comprises crates for storing the insect larvae, wherein the crates are stackable to form a vertical column and wherein the crates comprise lateral cutouts disposed on opposite sides. An air inlet duct for individually providing conditioned air to the crates is disposed in a vertical direction and comprises at least one nozzle for each crate in a column. The position of the at least one nozzle corresponds to the position of the lateral cutout of the respective crate. The system further comprises an air outlet duct, wherein the air outlet duct is disposed in a vertical direction and wherein the air outlet duct is disposed on a side of the stacked crates opposite to the air inlet duct.

Preferably, the air is conditioned to have a specific temperature, humidity, speed/pressure and/or $CO_2$ proportion. The air inlet duct may be formed of a bellow to provide uniform air pressure to each crate. The air inlet duct may comprise three or five nozzles per crate. The air inlet duct may provide conditioned air to two columns of stacked crates which are positioned opposite to each other with respect to the air inlet duct.

Preferably the air outlet duct is formed by a space between two adjacent columns of crates. Two columns of stacked crates each may have one air inlet duct to provide conditioned air in between and two air outlet ducts on the respective outsides of the columns. A suction force may be provided to suction the exhaust air through the air outlet ducts. Preferably a space is formed above the air outlet ducts to provide a uniform suction force to all air outlet ducts.

The invention will be described with reference to the accompanying figures.

Figure 1:
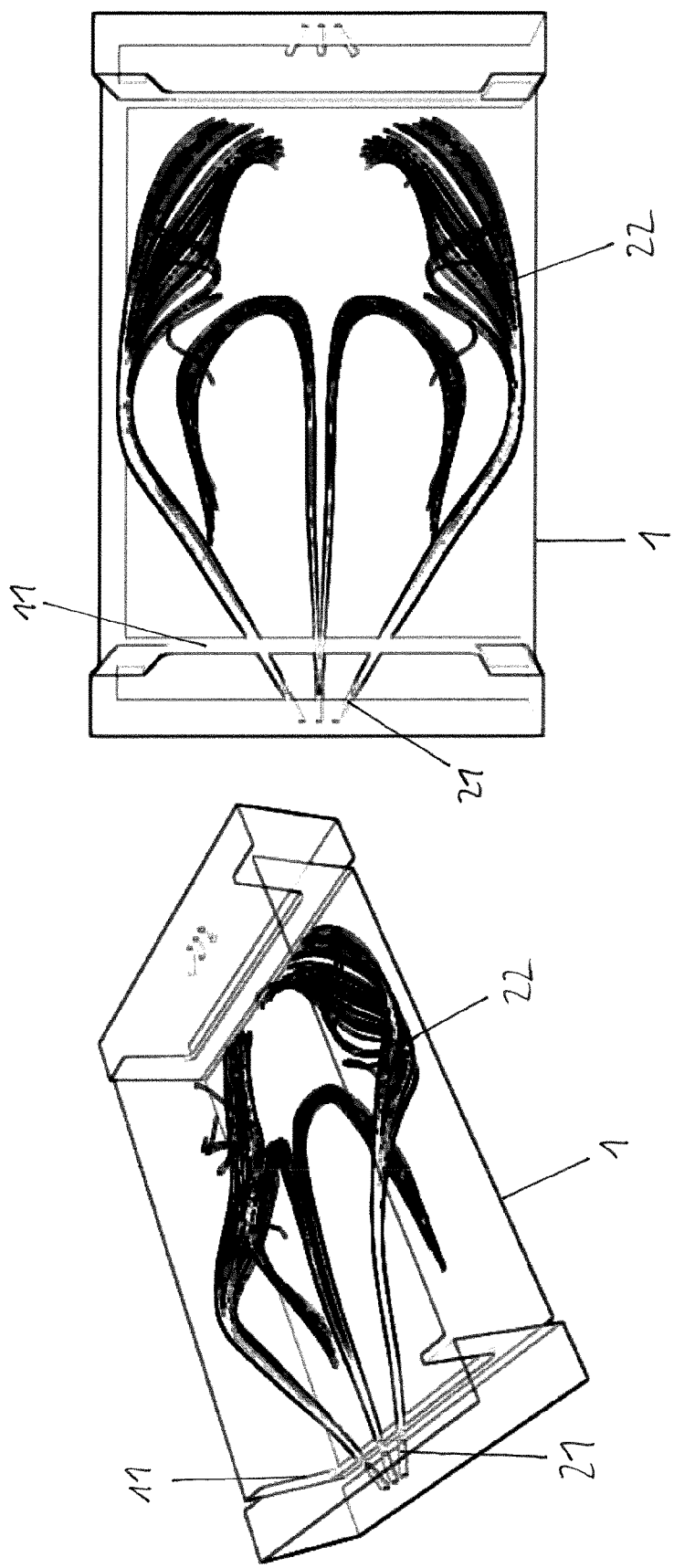
FIG. 1 shows a CFD simulation of the air flow through a crate

The invention concerns a heating, ventilation and air conditioning (HVAC) system directed towards providing a suitable environment for rearing of insect larvae. The larvae may grow on a substrate which provides nutrition, i.e. a nutritive medium. The medium may comprise organic waste or other types of nutrition which is suitable for insect larvae and allows them to grow. Thereby, the substrate itself contains microorganism that also grow and produce heat and $CO_2$. The larvae together with the substrate are stored in stackable crates 1, which may be rectangular. The walls of the crates 1 themselves are preferably airtight. The crates 1 are stacked to form a column and a plurality of columns is stored adjacent to each other to form rows. Multiple rows may be stored adjacent to each other, thus forming walls and corridors.

Stackability is achieved e.g. by self-centring elements on the crate walls which allow them to be stacked vertically and thereby roughly seal them in an airtight manner. However, other means to allow the crates 1 to be vertically stacked may be provided. Preferably, a column of crates 1 comprises between three and thirty crates 1. Thereby high-density of larvae and a large production quantity are achieved.

Since the larvae have to be supplied with fresh air, cutouts 11 are formed in the crates 1 to allow air to pass through. The cutouts 11 are formed on opposite sides, preferably on the shorter sides, but may also be provided on all four sides. The cutouts 11 may thus be disposed laterally.

The crates 1 are preferably about 290 mm high and have a height from the bottom of the crate 1 to the cutout 11 of at least 150 mm, in order to allow a substrate or nutritive medium height of 100 mm. More preferably the height from the bottom of the crate 1 to the cutout 11 is 160 mm which leads to a cutout 11 height of 130 mm. The width of the cutout 11 thereby is preferably 450 mm. The area of the cutout 11 may thus be approximately 58500 mm². The crates preferably have a length of 300-1200 mm, a width of 200-800 mm and a height of 100-500 mm. The crates 1 may have structural features, such as grooves and protrusions, which allow them to be stackable. Furthermore, the crates 1 may each include an RFID chip, a barcode, a QR code or the like which allow an identification of the crate 1 and automated processing.

However, when the crates 1 are simply stacked in a room to form rows and columns and the room is ventilated by conventional fans, it is difficult to provide a homogenous airflow through the crates 1, especially if the number of crates 1 is increased in order to scale up the rearing. Thus, the present invention provides a directed air flow over each individual crate 1. Furthermore, the air may be carefully conditioned to ensure optimal temperature, moisture and $CO_2$ content in the air. Therefore, each crate 1 may have its own individual air supply.

According to the invention, an air inlet duct 2 is formed adjacent to a column of stacked crates 1 to provide conditioned air. The air inlet duct 2 may be disposed in a vertical direction, wherein vertical describes the direction perpendicular to the ground. The air inlet duct may 2 also be disposed in a horizontal direction, wherein horizontal describes the direction parallel to the ground. Air outlets, which may be designed as openings or nozzles 21 in the air inlet duct 2, are formed in intervals corresponding to the cutouts 11 of the crates 1 when in a stacked arrangement.

The nozzles are preferably arranged between 10-80 mm above the bottom line of the cutout 11. At least one opening and maximum ten openings are provided per crate 1, but one to five openings per crate 1 may be preferred. By designing the openings as nozzles 21, a directed air flow can be assured and an optimised heat distribution can be achieved. I.e., the nozzles 21 serve to direct and/or regulate the air flow. The diameter of the openings or nozzles 21 may be adaptable.

The crates 1 may be positioned behind each other and the nozzles 21 may provide multiple crates 1 with conditioned air. Thus, multiple columns of crates 1 may form a row in the direction of the airflow and the air will pass the crates sequentially in a horizontal direction. Thereby, one nozzle 21 and arrangement of nozzles 21, respectively may serve one to eight crates 1, preferably one to four crates 1 and most preferably only one crate 1. In other words, the area served by one nozzle 21 or arrangement of nozzles 21, respectively may be less than 2 $m^2$, preferably less than 1 $m^2$ and more preferably less than 0.5 $m^2$.

In order to ensure homogenous air pressure and flow rate of the conditioned air to each crate 1, the vertical air inlet duct 2 may be a flexible air duct, e.g. formed of a bellow or a sock. The bellow can for example be filled with pressurised air which is then delivered to the crates 1 via the nozzles 21. The bellow may have a circular cross section. If a bellow with circular cross section is used, the development of vortices inside the crate 1 may be avoided by arranging the nozzles 21 having an angular offset with respect to each other. But also other structures which are capable of evenly distributing air to each crate 1 with identical pressure and flow rate may be used for this purpose. There may be a pressurised chamber provided above the crate stack to ensure uniform distribution of air with respect to pressure, air flow and air parameters to all air inlet ducts 2. In case of a vertical air inlet duct 2, the bellow may be suspended from the ceiling. The nozzles 21 may be disposed on opposing sides of the air inlet duct 2 to be able to provide conditioned air to two columns of stacked crates 1 simultaneously. The air flow per crate may be less than 40 $m^3/h$, preferably less than 30 $m^3/h$, more preferably less than 20 $m^3/h$. Simulations have shown that an appropriate volumetric air flow per crate may be 13 $m^3/h$.

To find an optimum configuration, computational fluid dynamics (CFD) simulations have been performed. The use of one nozzle 21 which was directed perpendicular to the cutout 11 of the crate 1 led to a direct jet from inlet to outlet but seemed to have little interaction with the biomass. Other CFD simulations used three nozzles 21, wherein one was perpendicular to the cutout 11 of the crate 1 and the other two were each offset by 30° to the left and right, respectively. This yielded an even distribution and airflow through the crate 1 without flow leakage at the crate's cutout 11 opposite to the nozzles 21. Thus, an interaction with the biomass throughout the crate 1 was achieved. Also by increasing the number of nozzles 21 to five which were offset by 30° and 45°, respectively, a good flow distribution in the crate 1 was observed. Again, no leakage at the crate's cutout 11 occurred and thus a good interaction of the conditioned air with the biomass can be expected. The external nozzles 21, however, may create some recirculation phenomena. However, the present disclosure is not limited to one, three or five nozzles 21, but also other numbers and angles might be used.

Figure 2:
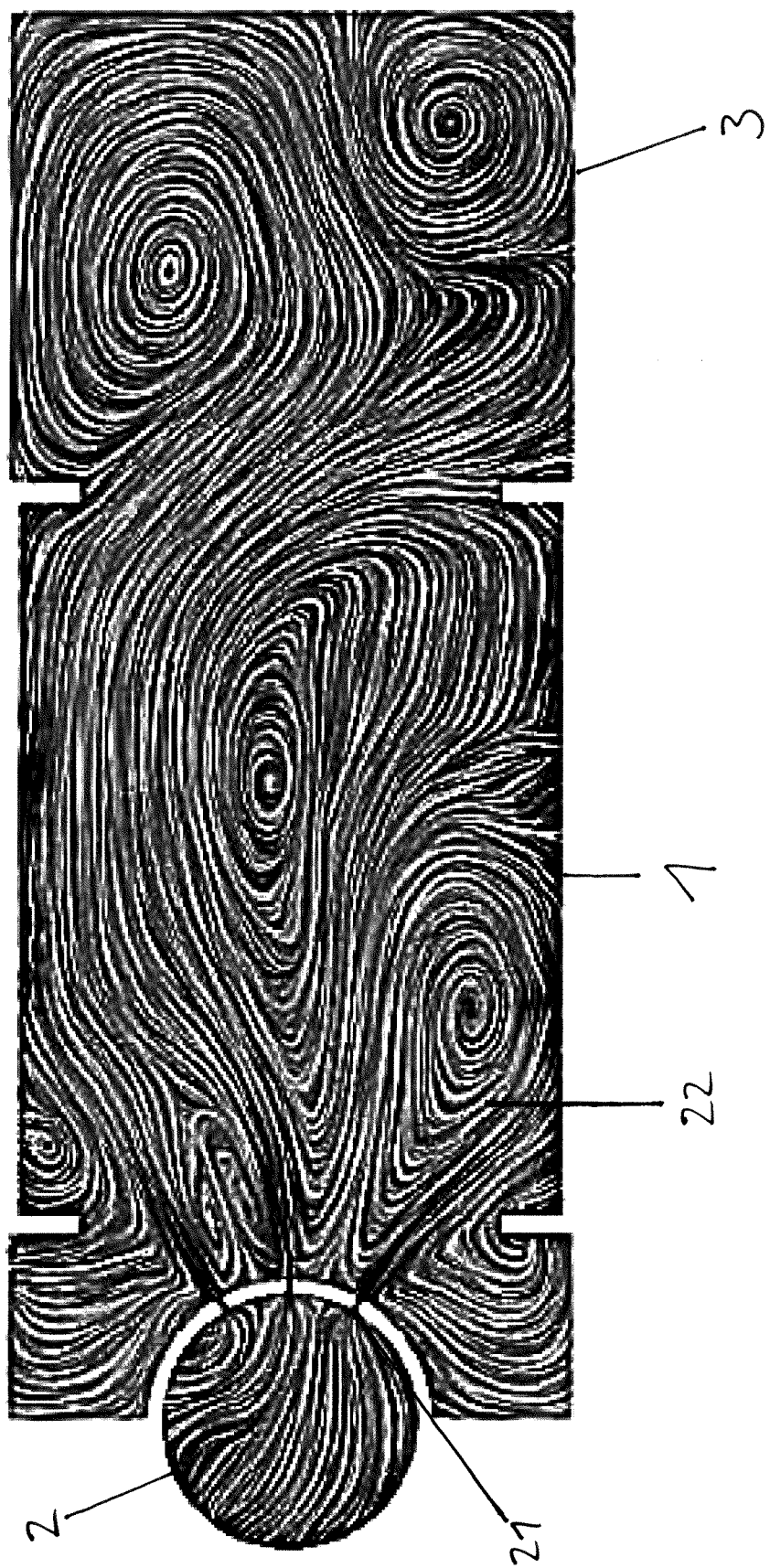
FIG. 2 shows a CFD simulation of the air flow through a crate

FIG. 1 shows the results of a CFD simulation using a simple model of crate 1 and three nozzles 21 from two different perspective views. As can be seen from the flow lines 22, the conditioned air is distributed over a majority of the volume of crate 1 and thus provides a homogenous growth climate. FIG. 2 is a top view of an air inlet duct 2, a crate 1 and an air outlet duct 3. In this simulation, a bellow with three nozzles 21, as described above, was used. Again, even distribution of conditioned air can be observed looking at the air flow lines 22.

One key aspect of efficient air conditioning and circulation is the transport of exhaust air, i.e. heat, moisture and $CO_2$, out of the room. Therefore, an air outlet duct 3 is formed by a space between two columns and rows of stacked crates 1 on a side of the crates 1 opposite to the air inlet duct 2. Since cutouts 11 are provided on at least two sides of the crates 1, the passing air can exit the crate 1 through the cutout 11 opposite to the air inlet duct 2.

Figure 3:
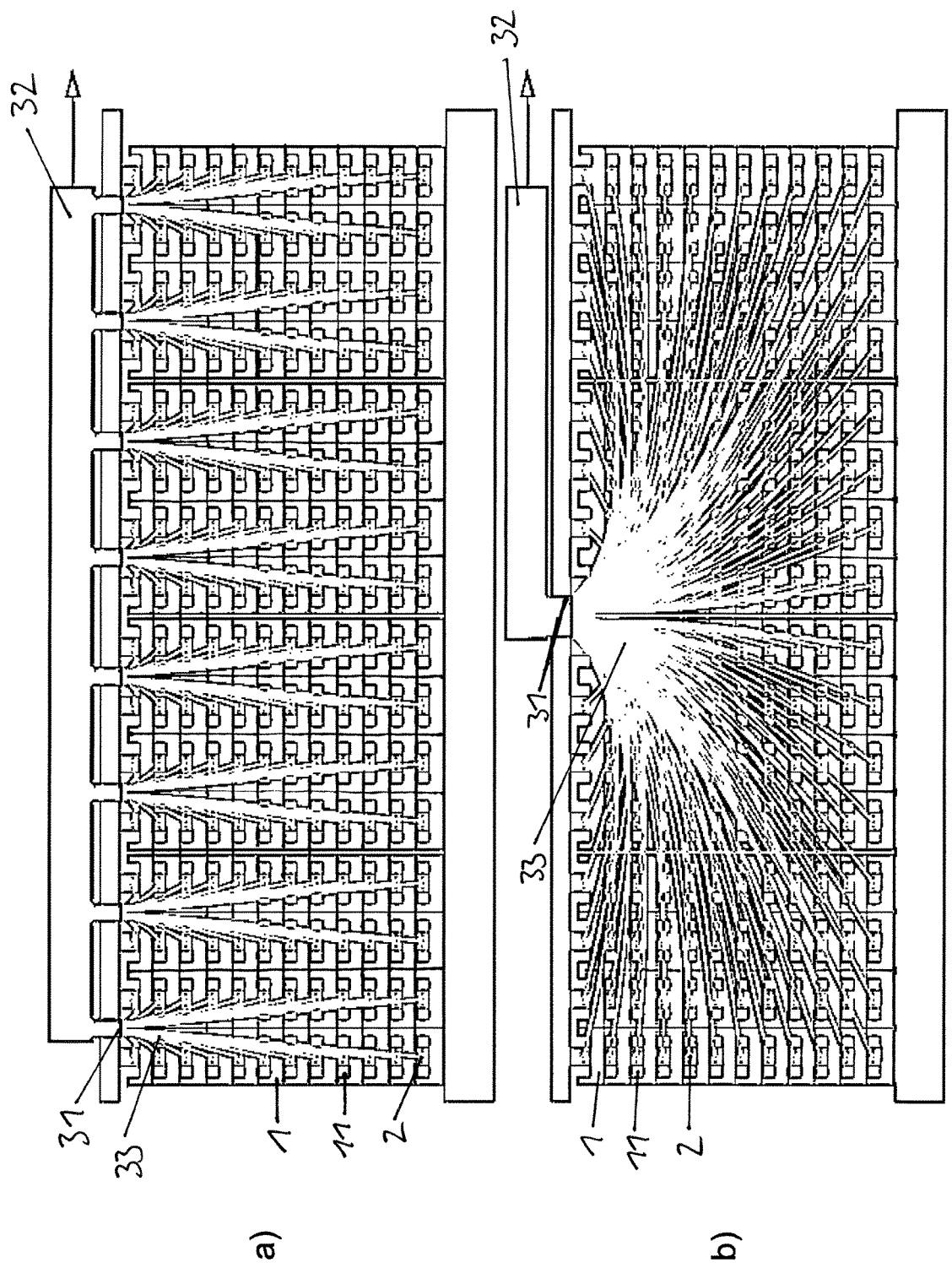
FIG. 3 shows exemplary structures of the exhaust system

At the ceiling of the conditioned room at least one opening 31 formed in an exhaust duct 32 is provided to suction the exhaust air out of the room. The respective air flow 33 is shown in FIGS. 3a) and b). The opening 31 may be formed as a single central exhaust opening 31 as shown in FIG. 3b). In case a plurality of openings is formed rather than a single central opening 31, the positions of the openings 31 preferably correspond to the air outlet ducts 3. With reference to FIG. 3a), CFD simulations have shown that a plurality of air outlet ducts 3 and respective openings 31, preferably one for two adjacent columns of crates 1, have yielded a preferred result. In order to efficiently suction the air out of the room, a suction force may be created. There is, however, the problem that the vacuum has to be uniformly distributed over all air outlet ducts 3.

In order to avoid the need for providing separate openings for each pair of columns, i.e. for each air outlet duct 3, a row of air outlet ducts 3 may be connected and provided with a single opening. In order to nevertheless provide a similar suction force for all air outlet ducts 3 in the row, and thus for all crates, the exhaust duct above the crates, i.e. the space above the crates leading the air from the outlet ducts to the opening, may be formed in a tapered form. In other words, the outlet ducts 3 are formed by a space between the columns of crates 1 while the exhaust ducts 32 are formed above the columns of crates 1 and are limited by the ceiling of the storage hall in which the crates 1 are located. The openings 31 thus are preferably formed in the ceiling of the storage hall. If a single central opening 31 should be used, the vacuum distribution between all air outlet ducts 3 may be improved by elevating the height of the exhaust duct 32, i.e. enlarging the volume above the crates. Thereby, the suction force at the outlet points in one rearing compartment formed of rows and columns of crates 1 may be unified. An uniform air flow rate for each crate may thus be achieved, since all outlet openings from the outlet channel have the same suction force.

Preferably, the exhaust air which has already passed the interior of the crate 1 is removed by a suction force providing a negative pressure to the air outlet duct 3. Also, the air outlet duct 3 formed by the stacked crates 1 may be wider than the air inlet duct 2. For example, the air outlet duct 3 may be between 200-1000 mm wide, more preferably 300-500 mm wide.

Hence, the outlet duct 3 may be formed of the space between stacked crates 1 and their walls, respectively, which form a channel, as well as ducts above the channel to provide a uniform suction force to the outlet channel.

Measurements of the inlet and exhaust air with respect to temperature, moisture and $CO_2$ may be performed in order to control the air conditioning and gather information about the insect larvae growth.

Figure 4:
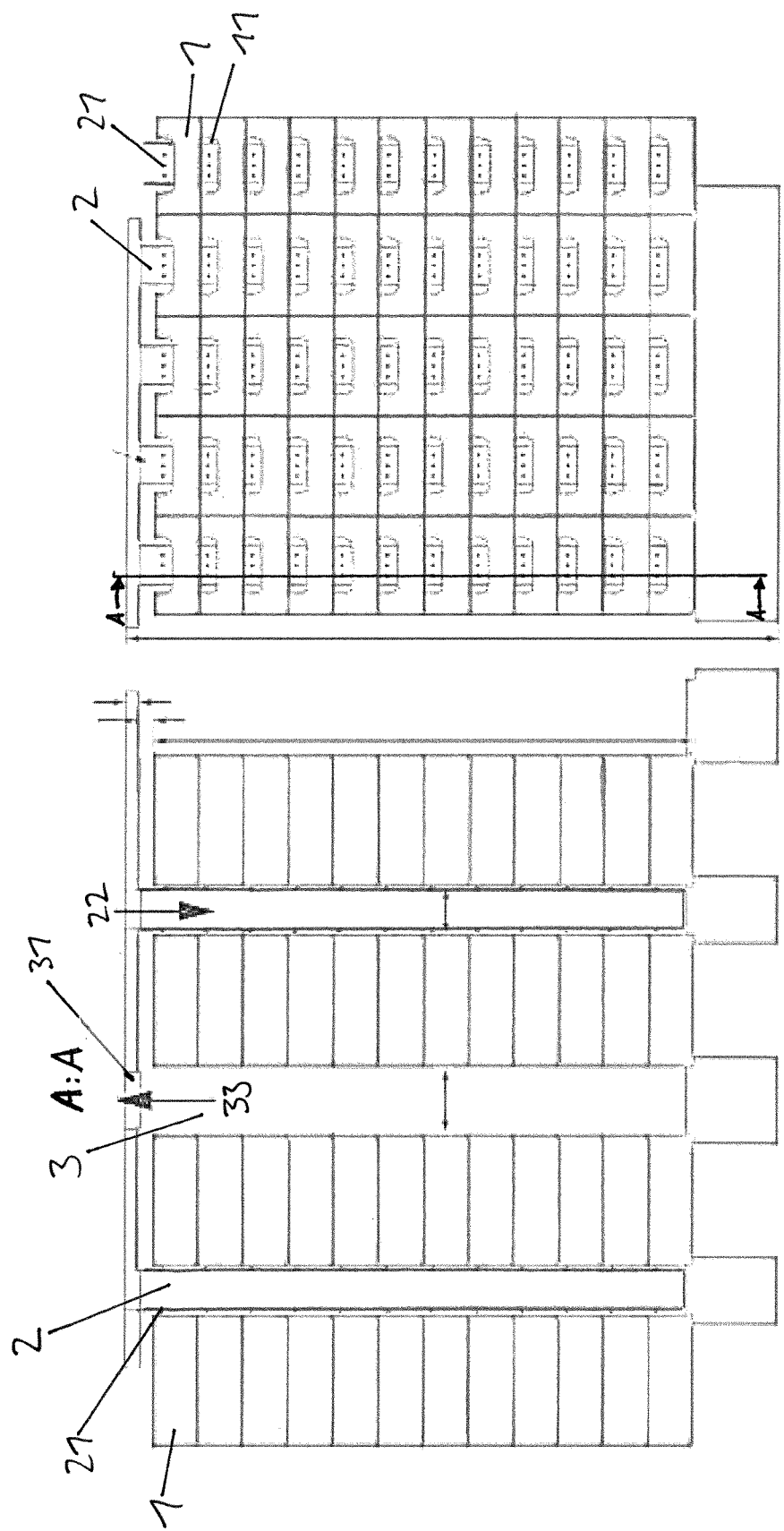
FIG. 4 shows an exemplary sectional view of the system according to the invention

FIG. 4 shows two sectional views through the air conditioned room which are offset by 90°. In this exemplary embodiment, the space between the columns forming the air inlet duct 2 and air outlet duct 3, respectively, are 300 mm and 400 mm. Depending on the size and total number of the crates 1 and their positioning inside the conditioned room, also other measures may be appropriate.

Figure 5:
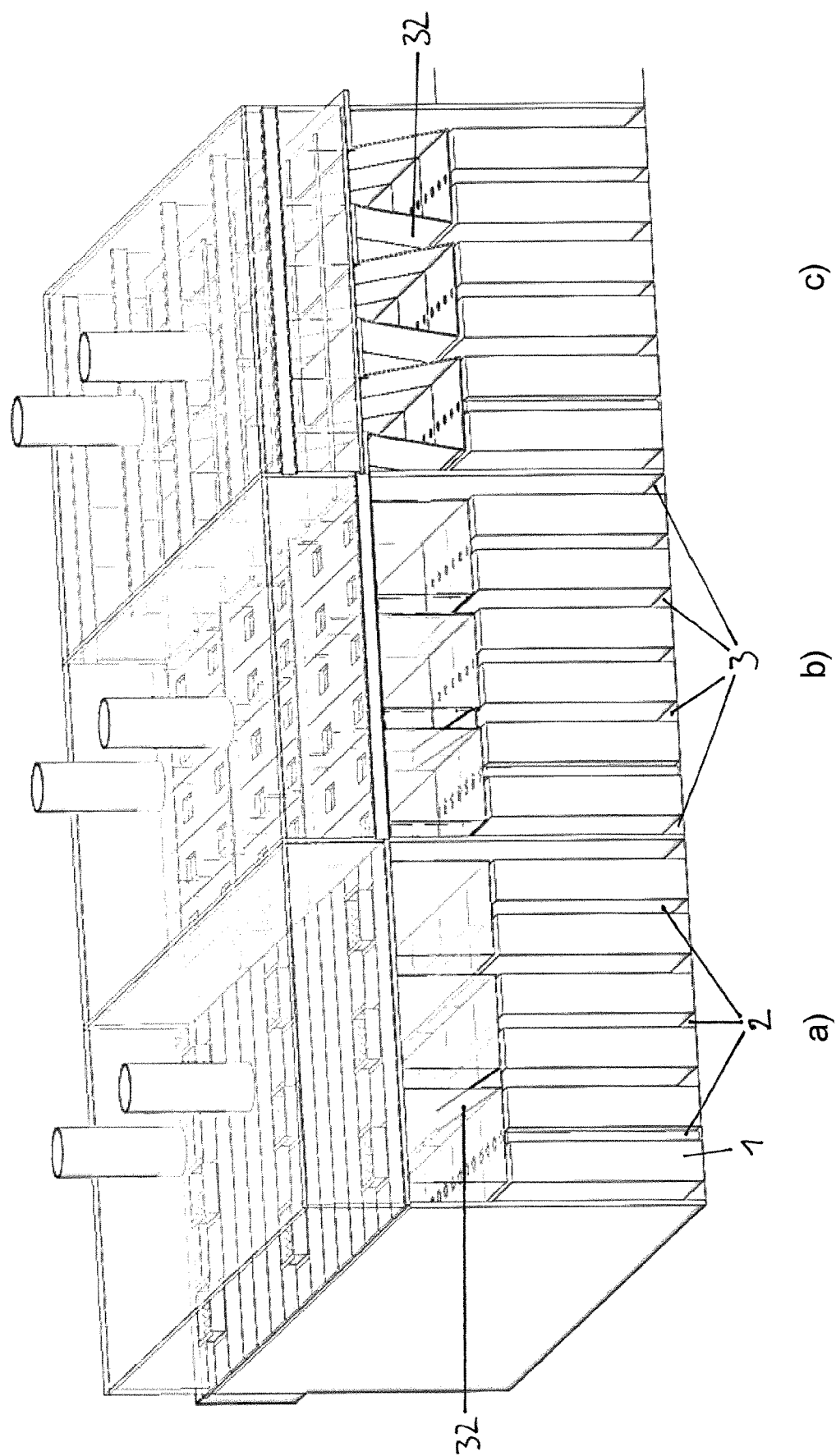
FIG. 5 shows an exemplary view of an air conditioned room according to the invention

FIG. 5 shows an exemplary arrangement of crates in an air conditioned room according to exemplary embodiments of the invention of three separate compartments with six lines of crates 1, each compartment having three air inlet ducts 2 and four air outlet ducts 3. Thus, the sequence in each compartment may be as follows: air outlet duct 3, crates 1, air inlet duct 2, crates 1, air outlet duct 3, in a repetitive manner so that each inlet duct 2 is shared by two columns of crates 1.

FIGS. 5 a) to c) show three exemplary embodiments of the invention which differ in the structure of the exhaust duct 32. FIGS. 5a) and b) both show a tapered exhaust duct 32 as explained above. In the compartment of FIG. 5c) the elevated ceiling of the exhaust duct 32 is depicted. Furthermore, three different structures of fresh air supply are shown in FIG. 5.

The effectiveness and performance of the present invention is not affected if some of the rows or columns of crates 1 are not in place. Thus, although a higher density of crates 1 and therefore a larger quantity of insect larvae can be conditioned at the same time, it is not necessary for the system to work properly to always have the room completely filled with crates 1.

Figure 6:
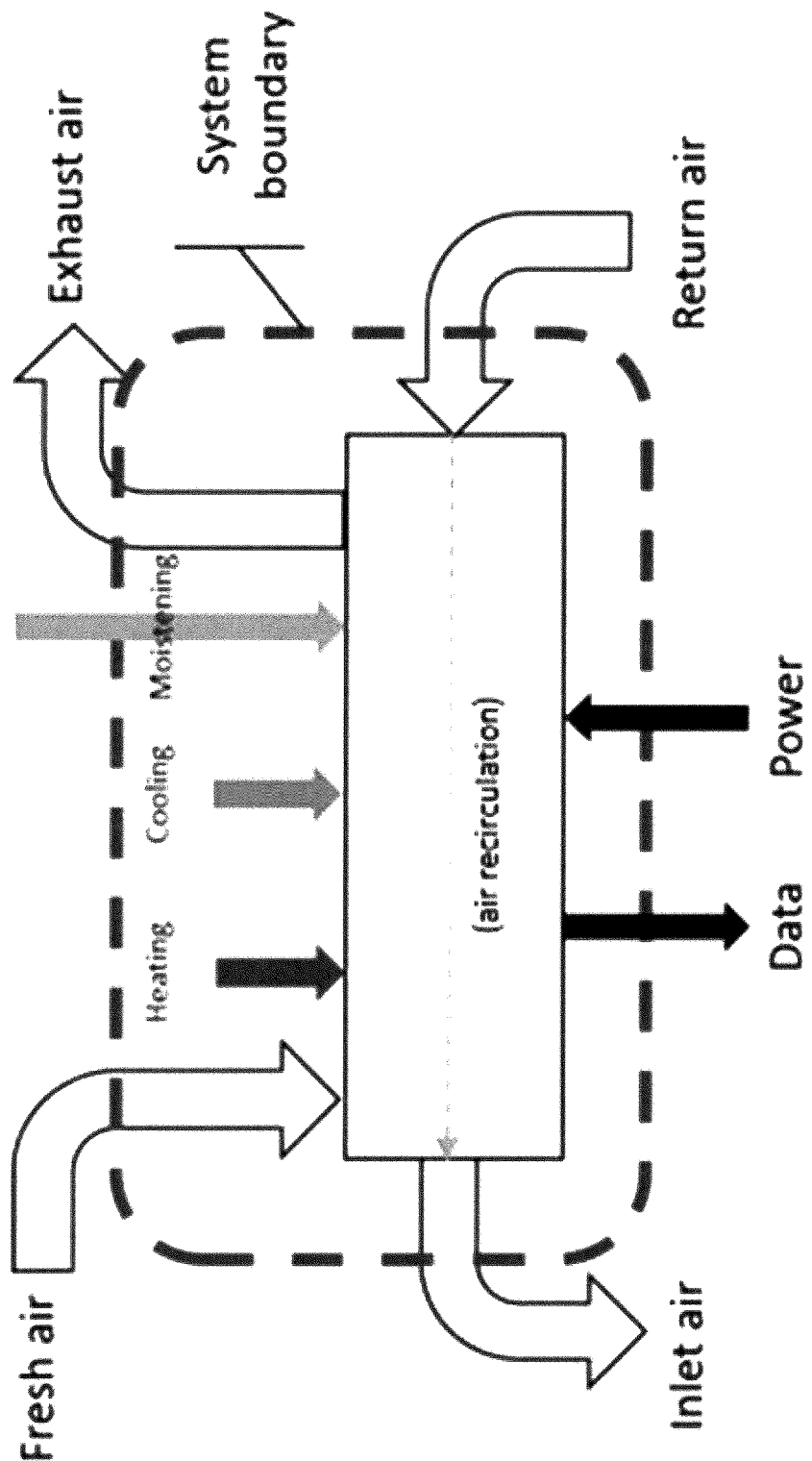
FIG. 6 shows a schematic system diagram.

FIG. 6 is a schematic system diagram illustrating the air flow according to an embodiment the present invention. Return air from the conditioned rearing room may be mixed with fresh air and conditioned with respect to different parameters such as temperature (heating/cooling), $CO_2$ content, $O_2$ content and moisture. The conditioned air is supplied to the room as inlet air where it provides a healthy growth climate for the insect larvae. The return air coming from the rearing room may be partially recirculated and partially discharged to the environment as exhaust air. The recirculation rate may be between 0-100%, depending on the conditions of the internal and external air. A power supply is provided to drive the air conditioning system. The measured data about the condition of the air, such as temperature, moisture and $CO_2$ content, is returned from the conditioning system and used to control said system and adapt the parameters if necessary in order to always have an optimal climate inside the room. The measurement points or sensors may be disposed in the inlet duct 2, the outlet duct 3 or the crate 1 itself. A controller may be provided to analyse the parameters of the incoming and/or outcoming air and adapt the conditioned air correspondingly.

In summary, according to the invention it is possible to efficiently provide an optimal growth climate homogenous to a large quantity of insect larvae. Upscaling of air circulation using conventional fans is only feasible up to a certain density of the crates in the room. By directing the airflow directly over each individual crate instead of circulating the air by conventional fans and carefully conditioning the air, the substrate to air energy transfer is optimised and high density rearing of insect larvae is feasible. Furthermore, the system extracts the air from the room to prevent heat and moisture from building up. Thus, uniform and healthy growth of the insect larvae is possible while reducing the amount of energy used. In case of illness of some of the animals, only single crates may be extracted without affecting the rest of the crates, since there is an individual airflow to and from each crate. By designing the air inlet duct as a bellow or sock, equal and homogenous airflow through each crate is assured. The crates may also be conditioned using a fluid. For example, a water circuit which is connected to each individual crate may be provided.

LIST OF REFERENCE SIGNS

1 Crate
11 Cutout
2 Air inlet duct
21 Nozzle
22 Fresh air flow
3 Air outlet duct
31 Exhaust opening
32 Exhaust duct
33 Exhaust air flow

The invention claimed is:

1. A system that provides conditioned air to a room for rearing insect larvae, the system comprising:
a plurality of crates that store the insect larvae, wherein each of the plurality of crates are stacked in the room and atop one another to form a vertical column of stacked crates, each of the plurality of crates comprising a pair of lateral cutouts disposed on opposite sides thereof,
an air inlet duct that provides conditioned air to each of the plurality of crates that form the vertical column of stacked crates, wherein the air inlet duct comprises at least one nozzle for each crate in the vertical column, wherein the position of the at least one nozzle corresponds to a position of a first of the pair of lateral cutouts of each respective crate in the vertical column, and
wherein a plurality of vertical columns of stacked crates are positioned to form at least one row of stacked crates each of the stacked crates is provided with conditioned air via a respective at least one nozzle,
an air outlet duct, wherein the air outlet duct is formed by a void formed between two columns of stacked crates, the air outlet duct disposed on a side of the columns of stacked crates opposite to the air inlet duct,
wherein the air outlet duct is communicatively connected with a respective exhaust duct disposed at a position above the air outlet duct;
wherein a suction force is provided to suction exhaust air through the air outlet duct via the exhaust duct,
wherein an upper space disposed above a ceiling of the room is formed above the exhaust duct and the air outlet duct and below a ceiling of a storage compartment to provide the suction force to the exhaust duct and the air outlet duct, the storage compartment including the room and the upper space, and
wherein the air outlet duct and the exhaust duct are connected with at least one opening formed in the ceiling of the room and to an air conditioning unit that suctions the exhaust air from the room into the upper space, at least a portion of the exhaust air being exhausted and discharged from the upper space and to an outside environment.

2. The system according to claim 1, wherein the air is conditioned to one or more of a specific temperature, humidity, speed/pressure, $O_2$ proportion and/or $CO_2$ proportion.

3. The system according to claim 1, wherein each of the plurality of the air inlet ducts comprises a bellows that provides a uniform air pressure to each crate.

4. The system according to claim 1, wherein each crate receives from 3 to 5 nozzles that extend from the air inlet duct.

5. The system according to claim 1, wherein the air inlet duct provides conditioned air to at least two vertical columns of stacked crates, the at least two vertical columns of stacked crates being positioned opposite to each other with respect to the air inlet duct.

6. The system according to claim 1, wherein at least two vertical columns of stacked crates each utilize a common air inlet duct to provide conditioned air, the air inlet duct disposed between the two vertical columns, and two air outlet ducts are disposed on the respective sides of the vertical columns opposite the air inlet duct.

7. The system according to claim 1, wherein when a plurality of air outlet ducts are provided, each of the plurality of air outlet ducts are connected with the at least one opening formed in the ceiling of the room to suction the exhaust air from the room into the upper space, and a uniform suction force is applied to each of the plurality of air outlet ducts.

8. A system for rearing insect larvae, the system comprising:
- a plurality of crates that house the insect larvae, each of the plurality of crates including a bottom wall and a pair of oppositely disposed side walls, each of the oppositely disposed side walls including a cutout portion that forms an opening, the plurality of crates stacked atop one another to form a vertical column;
- an air inlet duct that provides conditioned air to each of the plurality of crates stacked atop one another, the air inlet duct comprising a plurality of nozzles extending therefrom such that a respective one of each of the plurality of stacked crates forming the vertical column receives at least one nozzle proximate the cutout portion;
- wherein, a plurality of vertical columns of stacked crates are positioned to abut one another to form at least one horizontal row of stacked crates, each of the stacked crates forming the at least one horizontal row receiving conditioned air from a respective one of the plurality of nozzles;
- wherein, a plurality of horizontal rows of stacked crates are non-abuttingly positioned relative to one another so as to form an air outlet duct therebetween, the air outlet duct disposed on a side of the plurality of horizontal rows of stacked crates that is opposite to the side corresponding to the air inlet duct;
- wherein, the air outlet duct is communicatively connected to an exhaust duct;
- wherein, a suction force is provided to suction exhaust air through the air outlet duct via the exhaust duct;
- wherein, when a plurality of air outlet ducts are formed from a plurality of non-abuttingly positioned horizontal rows, a respective exhaust duct is disposed above each of the plurality of air outlet ducts and below a ceiling of an enclosure housing the plurality of crates, and a uniform suction force is applied to the plurality of air outlet ducts by an air conditioning unit; and,
- wherein, each of the respective exhaust ducts is formed from a pair of walls.

9. A system that provides conditioned air to a room for rearing insect larvae, the system comprising:
- a plurality of crates that store the insect larvae, wherein each of the plurality of crates are stacked in the room and atop one another to form a plurality of vertical columns of stacked crates, each of the plurality of crates comprising a pair of lateral cutouts disposed on opposite sides thereof, wherein the plurality of vertical columns of stacked crates are positioned to form a plurality of rows of stacked crates,
- a plurality of air inlet ducts that provide conditioned air to each of the plurality of crates that form the plurality of vertical columns and plurality of rows, wherein each of the plurality of air inlet ducts comprises at least one nozzle for each crate in the plurality of vertical columns and plurality of rows, wherein the position of the at least one nozzle corresponds to a position of a first of the pair of lateral cutouts of each respective crate in the plurality of vertical columns and plurality of rows, and
- a plurality of air outlet ducts, wherein each of the plurality of air outlet ducts is formed by a void formed between columns of stacked crates, each of the plurality of air outlet ducts disposed on a side of the columns of stacked crates opposite to the plurality of air inlet ducts,
- wherein each of the plurality of air outlet ducts is connected with a respective one of a plurality of exhaust ducts disposed above the air outlet ducts;
- wherein a suction force is provided to suction exhaust air through each of the plurality of air outlet ducts via a respective one of the plurality of exhaust ducts,
- wherein an upper space disposed above a ceiling of the room is formed above the plurality of exhaust ducts and the plurality of air outlet ducts and below a ceiling of a storage compartment to provide the suction force to the plurality of exhaust ducts and the plurality of air outlet ducts, the storage compartment including the room and the upper space,
- wherein the plurality of air outlet ducts and the plurality of exhaust ducts are connected with at least one opening formed in the ceiling of the room and to an air conditioning unit that suctions the exhaust air from the room into the upper space, at least a portion of the exhaust air being exhausted and discharged from the upper space and to an outside environment, and
- wherein at least one of the plurality of exhaust ducts is tapered and extends between a respective air outlet duct and a ceiling of the room.

* * * * *